(12) United States Patent
Bu et al.

(10) Patent No.: US 9,663,542 B2
(45) Date of Patent: May 30, 2017

(54) O-PHENYL CHALCONE COMPOUNDS AND PREPARATION METHOD AND USE THEREOF

(71) Applicant: Sun Yat-Sen University, Guangzhou (CN)

(72) Inventors: Xianzhang Bu, Guangzhou (CN); Cuige Zhu, Guangzhou (CN); Xin Yue, Guangzhou (CN); Yinglin Zuo, Guangzhou (CN); Yu Chen, Guangzhou (CN); Gesi Wen, Guangzhou (CN)

(73) Assignee: Sun Yat-Sen University (CN)

( * ) Notice: Subject to any disclaimer, the term of this patent is extended or adjusted under 35 U.S.C. 154(b) by 0 days.

(21) Appl. No.: 15/218,738

(22) Filed: Jul. 25, 2016

(65) Prior Publication Data

US 2016/0333033 A1 Nov. 17, 2016

Related U.S. Application Data

(63) Continuation of application No. PCT/CN2015/070651, filed on Jan. 14, 2015.

(30) Foreign Application Priority Data

Jan. 23, 2014 (CN) .......................... 2014 1 0032845

(51) Int. Cl.

| | | |
|---|---|---|
| *C07C 255/56* | (2006.01) |
| *C07C 51/373* | (2006.01) |
| *C07C 45/63* | (2006.01) |
| *C07C 253/30* | (2006.01) |
| *C07C 303/22* | (2006.01) |
| *C07C 309/44* | (2006.01) |
| *C07C 225/22* | (2006.01) |
| *C07C 65/38* | (2006.01) |
| *C07C 49/84* | (2006.01) |
| *C07D 295/12* | (2006.01) |
| *C07D 207/08* | (2006.01) |
| *C07F 9/12* | (2006.01) |
| *C07C 49/835* | (2006.01) |
| *C07F 5/02* | (2006.01) |
| *C07C 45/45* | (2006.01) |
| *C07C 51/347* | (2006.01) |
| *C07C 221/00* | (2006.01) |

(52) U.S. Cl.
CPC ................ *C07F 9/12* (2013.01); *C07C 45/45* (2013.01); *C07C 45/63* (2013.01); *C07C 49/835* (2013.01); *C07C 49/84* (2013.01); *C07C 51/347* (2013.01); *C07C 51/373* (2013.01); *C07C 65/38* (2013.01); *C07C 221/00* (2013.01); *C07C 225/22* (2013.01); *C07C 253/30* (2013.01); *C07C 255/56* (2013.01); *C07C 303/22* (2013.01); *C07C 309/44* (2013.01); *C07D 207/08* (2013.01); *C07D 295/12* (2013.01); *C07F 5/025* (2013.01)

(58) Field of Classification Search
CPC ..... C07C 51/373; C07C 45/63; C07C 253/30; C07C 303/22; C07C 45/45; C07C 309/44; C07C 225/22; C07C 65/38; C07C 49/84; C07D 295/12; C07D 207/08; C07F 9/12
See application file for complete search history.

(56) References Cited

FOREIGN PATENT DOCUMENTS

| CN | 102344351 A | 2/2012 |
| NZ | 198879 A | 2/1985 |
| PT | 73973 A | 12/1981 |

OTHER PUBLICATIONS

Zuo et al., European Journal of Medicinal Chemistry, 2012, 50, 393-404.*
Zuo et al., 2012, caplus an 2012:415944.*
Zhu et al.,"Discovery of potent cytotoxic ortho-aryl chalcones as new scaffold targeting 1, 2, 4-10 tubulin and mitosis with affinity-based fluorescence", Journal of Medicinal Chemistry, Jul. 25, 2014 (Jul. 25, 2014), see pp. 6364-6382.
International Search Report for Application No. PCT/CN2015/070651 dated Mar. 23, 2015. (English translation is at the end.).

* cited by examiner

*Primary Examiner* — Sun Jae Yoo
(74) *Attorney, Agent, or Firm* — Lerner, David, Littenberg, Krumholz & Mentlik, LLP

(57) ABSTRACT

Disclosed are an o-phenyl chalcone compounds and preparation methods and uses thereof. The o-phenyl chalcone compounds are capable of inhibiting the aggregation of microtubules in tumor cells and influencing the mitosis of the cells, and have a high antitumor activity. The compounds also have inhibitory activity against proliferation on various tumor cells, such as a human ovary cancer cell A2780, a human colon cancer cell HCT8, a human breast cancer cell MCF7, a human lung cancer cell A549, a human colon cancer cell SW480, a human nasopharyngeal carcinoma cell CNE2, a human liver cancer cell HepG2 and the like at nanomole concentrations.

4 Claims, 1 Drawing Sheet

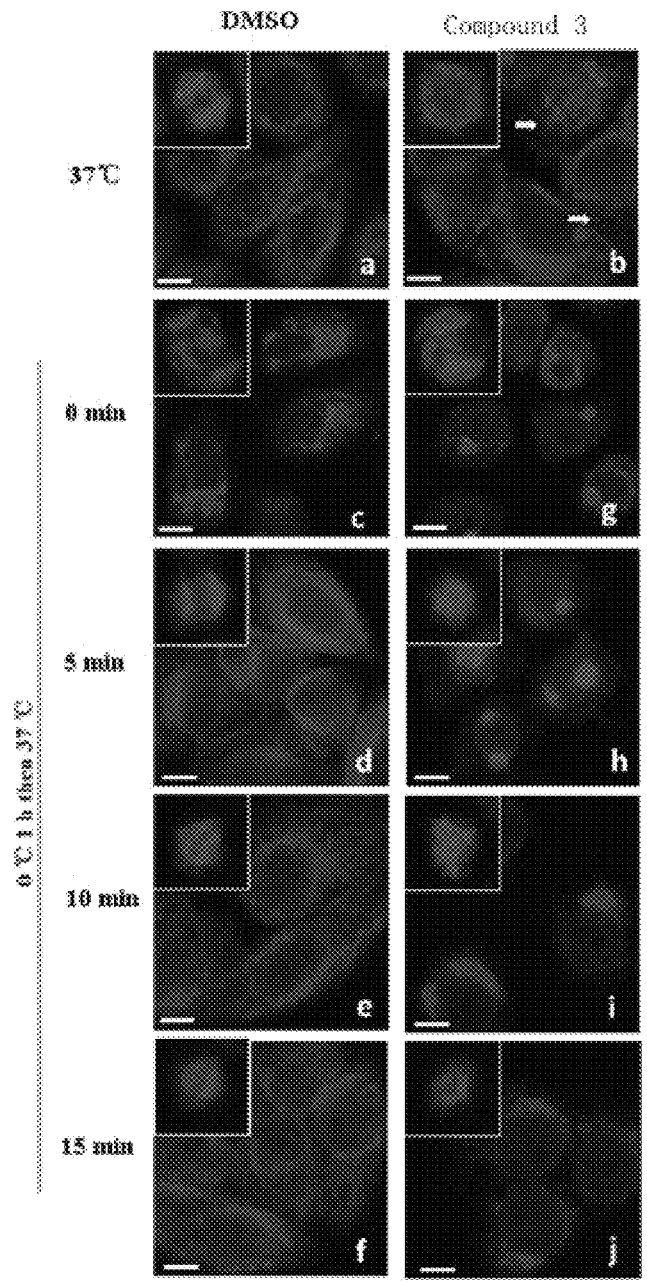

O-PHENYL CHALCONE COMPOUNDS AND PREPARATION METHOD AND USE THEREOF

CROSS-REFERENCE TO RELATED APPLICATION

The present application is a continuation of International Application No. PCT/CN2015/070651 filed Jan. 14, 2015, which claims priority from Chinese Patent Application No. 201410032845.9 filed Jan. 23, 2014, the disclosures of which are hereby incorporated herein by reference.

FIELD OF THE INVENTION

The present invention is in the field of medicinal chemistry, and particularly relates to o-phenyl chalcone compounds and preparation methods and uses thereof.

BACKGROUND OF THE INVENTION

Malignant tumors are diseases severely threatening human health. Chemotherapy continues to be an essential therapy for tumor treatments. Developing newly effective anti-tumor drug against effective anti-tumor targets is an important way to achieve effective tumor chemotherapy. Microtubules and tubulin are important anti-tumor targets, and representative drugs in clinic include paclitaxel, vinblastine, vincristine and the like. Paclitaxel promotes the aggregation of tubulin to form microtubules while the latters inhibit aggregation of tubulin, thereby disrupting mitosis to attain an effect of anti-tumor. Although drugs based on paclitaxel and vinblastine have been used in clinic, these drugs suffer some disadvantage factors including the rare resource, complex synthesis, high price or the like. Meanwhile, some molecules have been found to initiate tumor resistance.

Moreover, poor physical properties such as poor solubility exist in most of such molecules, which limits such drugs in clinical use. To overcome these drawbacks, it is important to design drugs with new structures, high activities, high bio-security and good physical properties for achieving microtubule targeted anti-tumor treatments.

A biaryl structure, for example bifendate, is a pharmacophore exists in natural products and various anti-tumor compounds with biaryl structure were literaturally reported. Chalcone compounds are widely found in nature and its basic skeleton structure is 1,3-diphenylcyclopropenone. Chalcone has been found to have activities including anti-inflammatory, anti-angiogenic, anti-microbial, anti-bacterial, anti-tumor activity and the like. It can be also used as optical recording materials, antidepressants and the like. However, naturally occurring chalcones still have drawbacks including low selectivity, generally low activity and the like. Highly active molecules which based on the structural model of chalcone with structural modifications has gained wide attention.

SUMMARY OF THE INVENTION

An object of the present invention is to provide an o-phenyl chalcone compound which have a high anti-cancer activity and can be used in preparation of anti-tumor drugs.

Another object of the present invention is to provide the preparation method for the o-phenyl chalcone compound.

Still another object of the present invention is to provide the use of the o-phenyl chalcone compound.

In some embodiments provided are o-phenyl chalcone compounds, specifically selected from a group consisting of the following molecular structures:

1
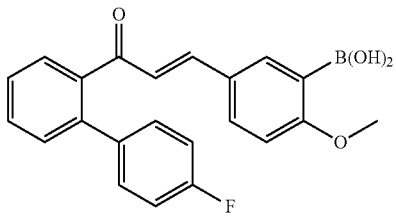

2
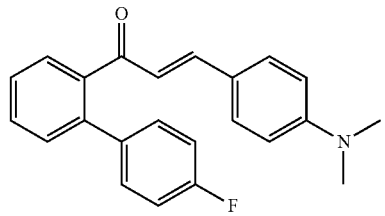

3
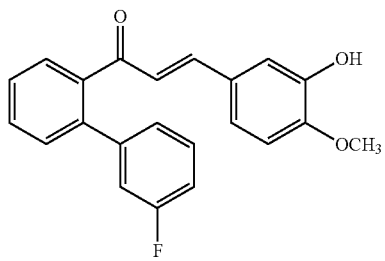

4
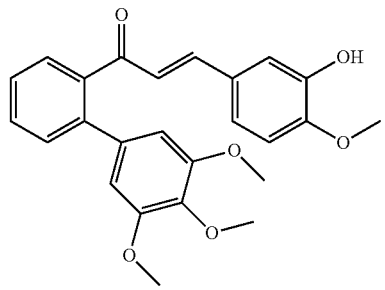

5
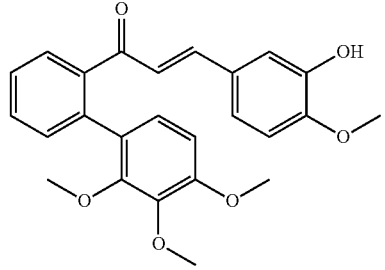

6
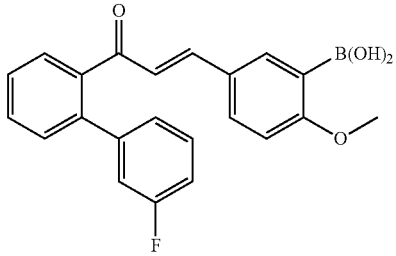

7
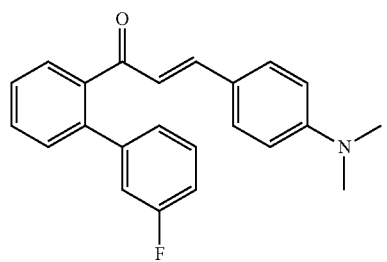
8
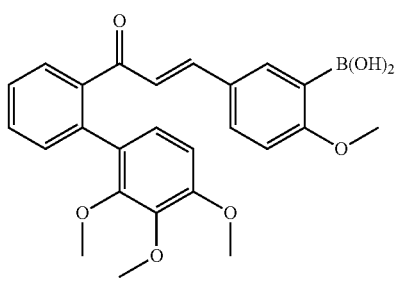
9
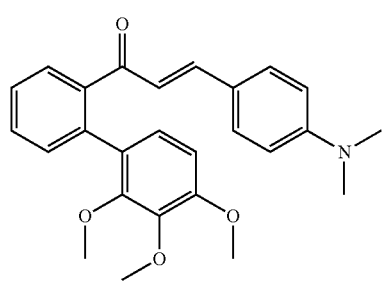
10
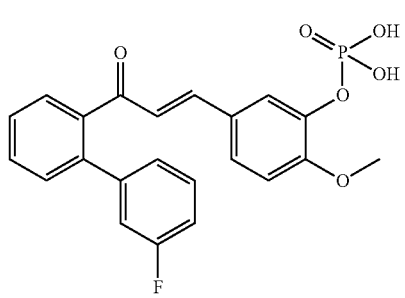
11
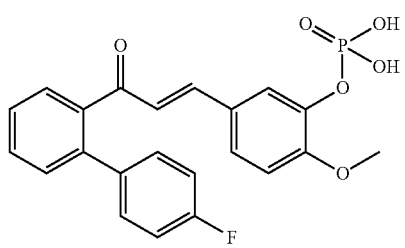
12
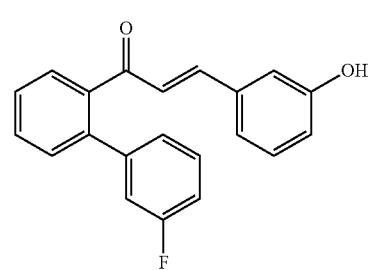
13
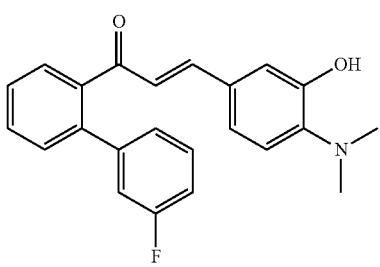
14
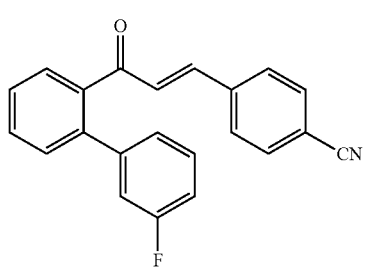
15
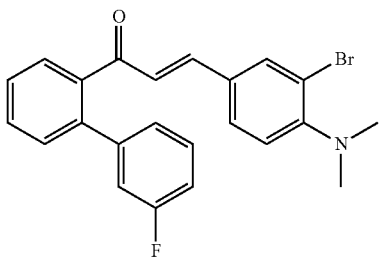
16
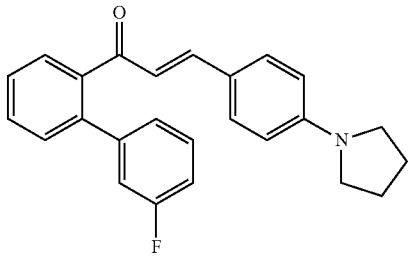
17
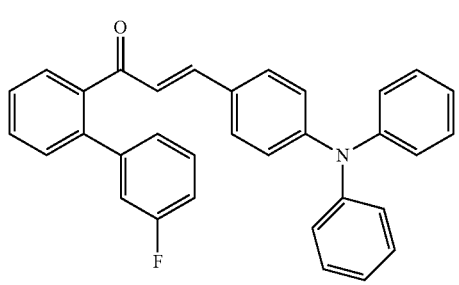
18
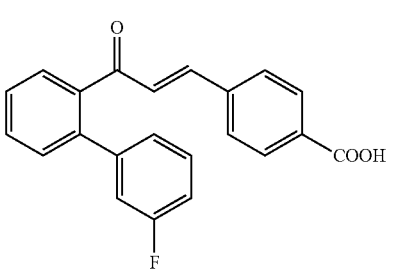

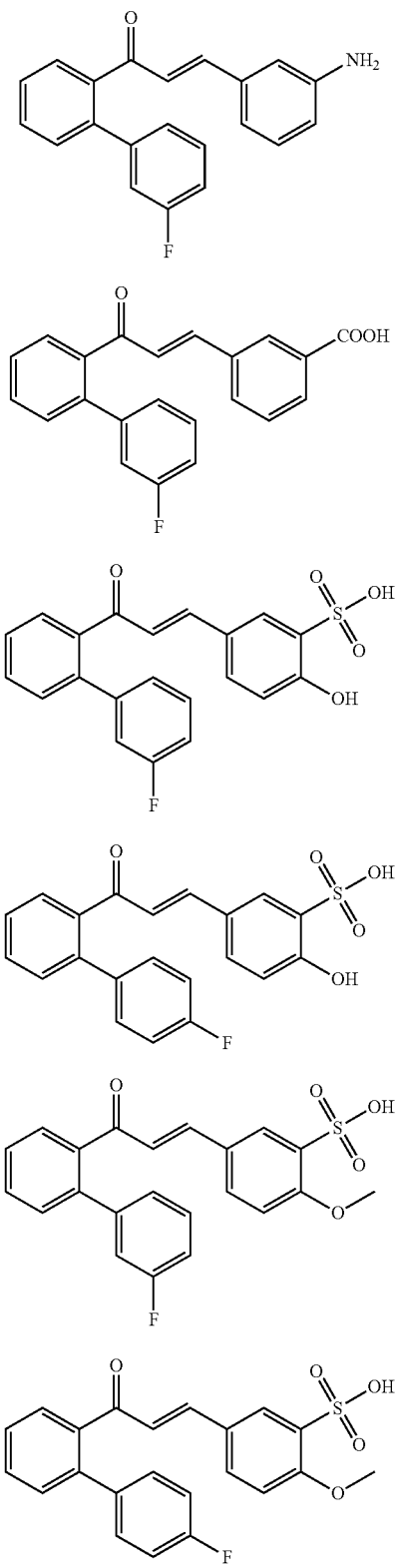

Chemical names of above compounds are provided as follows.

(E)-(5-(3-(4'-fluoro[1,1'-biphenyl]-2-yl)-3-oxoprop-1-en-1-yl)-2-methoxyphenyl) boronic acid (compound 1),
(E)-3-(4-(dimethylamino)phenyl)-1-(4'-fluoro[1,1'-biphenyl]-2-yl)prop-2-en-1-one (compound 2),
(E)-1-(3'-fluoro[1,1'-biphenyl]-2-yl)-3-(3-hydroxy-4-methoxyphenyl)prop-2-en-1-one (compound 3),
(E)-3-(3-hydroxy-4-methoxyphenyl)-1-(3',4',5'-trimethoxy[1,1'-biphenyl]-2-yl)prop-2-en-1-one (compound 4),
(E)-3-(3-hydroxy-4-methoxyphenyl)-1-(2',3',4'-trimethoxy[1,1'-biphenyl]-2-yl)prop-2-en-1-one (compound 5),
(E)-(5-(3-(3'-fluoro[1,1'-biphenyl]-2-yl)-3-oxoprop-1-en-1-yl)-2-methoxyphenyl)boronic acid (compound 6),
(E)-3-(4-(dimethylamino)phenyl)-1-(3'-fluoro[1,1'-biphenyl]-2-yl)prop-2-en-1-one (compound 7),
(E)-5-(3-(2',3',4'-trimethoxy[1,1'-biphenyl]-2-yl)-3-oxoprop-1-en-1-yl))-2-methoxy phenyl)boronic acid (compound 8)
(E)-1-(2',3',4'-trimethoxy[1,1'-biphenyl]-2-yl)-3-(4-(Dimethylamino)phenyl)prop-2-en-1-one (compound 9),
(E)-(5-(3-(3'-fluoro[1,1'-biphenyl]-2-yl)-3-oxoprop-1-en-1-yl)-2-methoxyphenol)phosphate ester (compound 10),
(E)-(5-(3-(4'-fluoro[1,1'-biphenyl]-2-yl)-3-oxoprop-1-en-1-yl)-2-methoxyphenol)phosphate ester (compound 11),
(E)-1-(3'-fluoro[1,1'-biphenyl]-2-yl)-3-(3-hydroxy)prop-2-en-1-one (compound 12),
(E)-1-(3'-fluoro[1,1'-biphenyl]-2-yl)-3-(3-hydroxy-4-(dimethylamino)phenyl)prop-2-en-1-one (compound 13),
(E)-1-(3'-fluoro[1,1'-biphenyl]-2-yl)-3-(4-cyanophenyl)prop-2-en-1-one (compound 14),
(E)-1-(3'-fluoro[1,1'-biphenyl]-2-yl)-3-(3-bromo-4-(dimethylamino)phenyl)prop-2-en-1-one (compound 15),
(E)-1-(3'-fluoro[1,1'-biphenyl]-2-yl)-3-(4-pyrrolidine-1-yl)prop-2-en-1-one (compound 16),
(E)-1-(3'-fluoro[1,1'-biphenyl]-2-yl)-3-(4-(diphenylamino)phenyl)prop-2-en-1-one (compound 17),
(E)-4-(3'-fluoro[1,1'-biphenyl]-2-yl)-3-oxoprop-1-en-1-yl benzoic acid (compound 18),
(E)-1-(3'-fluoro[1,1'-biphenyl]-2-yl)-3-(3-aminophenyl)prop-2-en-1-one (compound 19),
(E)-3-(3'-fluoro[1,1'-biphenyl]-2-yl)-3-oxoprop-1-en-1-yl benzoic acid (compound 20),
(E)-5-(3-(3'-fluoro[1,1'-biphenyl]-2-yl)-3-oxoprop-1-en-1-yl)-2-hydroxybenzenesulfonic acid (compound 21),
(E)-5-(3-(4'-fluoro[1,1'-biphenyl]-2-yl)-3-oxoprop-1-en-1-yl)-2-hydroxybenzenesulfonic acid (compound 22),
(E)-5-(3-(3'-fluoro[1,1'-biphenyl]-2-yl)-3-oxoprop-1-en-1-yl)-2-methoxybenzenesulfonic acid (compound 23), and
(E)-5-(3-(4'-fluoro[1,1'-biphenyl]-2-yl)-3-oxoprop-1-en-1-yl)-2-methoxybenzenesulfonic acid (compound 24).

Preparation methods of the compounds 1-9, 12, 14-24 include the following steps:

S1. Reacting 1-(2-bromophenyl)ethanone with corresponding boronic acid to form an intermediate product, S2. Reacting the intermediate product with corresponding benzaldehyde compounds by aldol condensation to form a target product.

A method for preparing the compound 10 include obtaining compound 3 by the above preparation method, contacting compound 3 with diethyl phosphate for phosphate esterification and removing the alkyl of phosphate ester to form the target compound.

A method for preparing compound 11 includes reacting a coupling product of 1-(2-bromophenyl) ethanone and (4-fluorophenyl) boronic acid with 3-hydroxy-4-methoxybenzaldehyde to obtain an intermediate, subjecting the intermediate and diethyl phosphite to phosphate esterification, and removing the alkyl of phosphate ester to form the target compound.

A method for preparing compound 13 includes obtaining compound 15 by the preparation method of claim 2, and subjecting compound 15 to substitution reaction under alkaline condition and using CuI as a catalyst to obtain the hydroxylated target product.

The intermediate is prepared by Suzuki-Miyaura reaction (Suzuki coupling reaction) between 1-(2-bromophenyl)ethanone and the corresponding boronic acid compound.

In a preferred embodiment, the Suzuki-Miyaura reaction is performed using [1,1'-bis(diphenylphosphino) ferrocene] dichloropalladium dichloromethane complex (DPPF) as a palladium catalyst, potassium carbonate as an alkali metal carbonate, and 1,4-dioxane as a solvent by microwave heating at 150° C. for 30 min.

As an example, a preparation method of compound 1 of the present invention specifically includes: obtaining an intermediate by Suzuki-Miyaura reaction between 1-(2-bromophenyl)ethanone and (4-fluorophenyl)borate using DPPF as a catalyst, and obtaining a final product compound 1 by reaction between the intermediate and 5-formyl-2-methoxybenzene boronic acid.

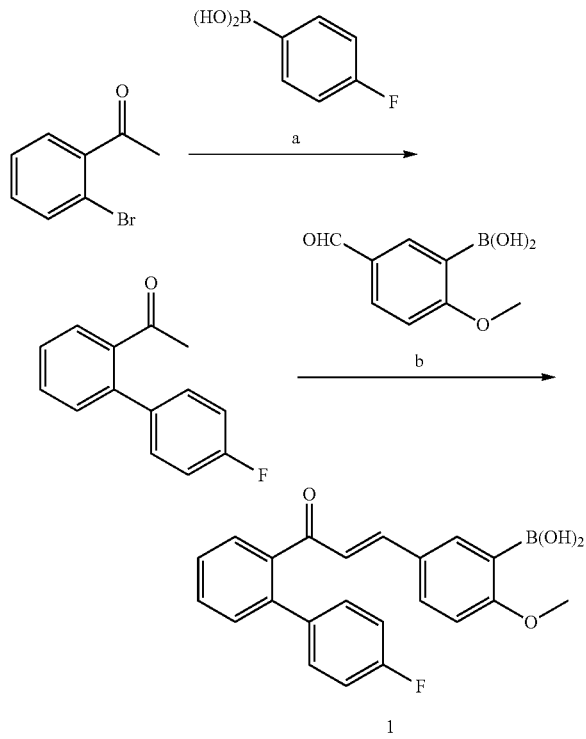

The present invention also provides use of the o-phenyl chalcone compounds in preparation of an anti-tumor drug.

The present invention also provides use of the o-phenyl chalcone compounds in preparation of an anti-tumor drug wherein the tumor is drug-resistant.

In a preferred embodiment, the drug-resistant tumor includes but is not limited to paclitaxel resistant tumor, vincristine resistant tumor, doxorubicin resistant tumor or cis-molybdenum resistant tumor.

In a preferred embodiment, the tumor includes but is not limited to ovarian cancer, colon cancer, breast cancer, lung cancer, nasopharyngeal cancer, or liver cancer.

The present invention also provides pharmaceutically acceptable salts formed by the o-phenyl chalcone compounds of the present invention.

In a preferred embodiment, the pharmaceutically acceptable salts include lithium salts, sodium salts, potassium salts, calcium salts, magnesium salts, iron salts, copper salts, organic ammonium salts, hydrochlorides, sulfates, phosphates, acetates, propionates, oxalates, citrates and the like.

The organic ammonium salts include methylamine salts, ethylamine salts, triethylamine salts, N,N-diisopropylethylamine salts and the like.

Through experiments, we found that the ortho-phenyl chalcone compounds of the present invention had high activity and good inhibitory effect on proliferation of cancel cells such as human ovarian cancer cells A2780, human colon cancer cells HCT8, human breast cancer cells MCF7, human lung cancer cells A549, human colon cancer cells SW480, human nasopharyngeal carcinoma cells CNE2, and human liver cancer cells HepG2, etc. The $IC_{50}$ values were detected to be lower than 133 nM, 153 nM, 88 nM, 128 nM, 86 nM, 87 nM and 93 nM respectively for the inhibitory effect on A2780, HCT-8, A549, MCF-7, CNE2, SW480 and HepG2. Meanwhile, anti-proliferative effects of the compounds of the present invention on the paclitaxel-resistant human ovarian cancer cell A2780/TAX, vincristine-resistant human colon cancer cell HCT8/VCT, and adriamycin-resistant human breast cancer cell MCF7/DOX were significantly better than that of colchicine, paclitaxel, doxorubicin, and vincristine which were used as four positive control pharmaceutical molecules.

In comparison with prior art, the present invention provides the following beneficial effect:

(1) the ortho-phenyl chalcone compounds of the present invention have high anti-tumor activity, and especially have significantly improved high proliferation inhibitory activity on a variety of tumor cells, such as human ovarian cancer cells A2780, human colon cancer cells HCT8, human breast cancer cells MCF7, human lung cancer cell A549, human colon cancer cells SW480, human nasopharyngeal carcinoma cells CNE2, human liver cancer cells HepG2 and the like, with the $IC_{50}$ mostly up to the level of nmol/L.

(2) the ortho-phenyl chalcone compounds of the present invention can effectively function against multi-drug-resistant tumors that are resistant against drugs in clinic such as paclitaxel, vincristine, doxorubicin or cis-molybdenum, etc.

(3) compared to representative drugs in clinic such as doxorubicin, paclitaxel, colchicine and vincristine, the ortho-phenyl chalcone compounds of the present invention not only have significant advantage with respect to anti-drug-resistant tumors, bot also have significant advantage with respect to physical properties and chemical properties, such as novel structure, simple synthesis, cheap raw materials, and good solubility.

BRIEF DESCRIPTION OF THE DRAWINGS

FIG. 1 shows the result of the active molecules of example 27 in inhibiting microtubule re-aggregation and disrupting co-aggregation of mitosis of cells on a cellular level, wherein a, c-f are solvent control groups added with 0.5% DMSO, and b, g-j are tested groups added with 31 nM of compound 3, and the showed scale bar is 10 μm.

DETAILED DESCRIPTION OF THE INVENTION

The present invention will now be described in more details in specific examples. However, the present invention is not limited by the specific examples. Unless otherwise specified, reagents and methods involved in the specific examples are reagents and methods commonly used in the art.

Example 1

Synthesis of (E)-(5-(3-(4'-fluoro[1,1'-biphenyl]-2-yl)-3-oxoprop-1-en-1-yl)-2-methoxyphenyl) boronic acid (compound 1)

A biphenyl intermediate (1-(4'-fluoro-[1,1'-biphenyl]-2-yl) ethanone (intermediate 1) was obtained by Suzuki-Miyaura reaction. To a microwave reaction vial were added 1-(2-bromophenyl) ethanone (199 mg, 1.0 mmol), (4-fluorophenyl) boronic acid (182 mg, 1.3 mmol), [1,1'-bis(diphenylphosphino) ferrocene]palladium dichloride dichloromethane complex (DPPF) (50 mg, 0.06 mmol), 2 M (aq) $K_2CO_3$ (1.5 ml), and 1,4-dioxane (1.5 ml). The reaction mixture was sealed and heated at 150° C. for 30 min. After the reaction mixture was cooled, water (10 mL) was added. The mixture was extracted three times with ethyl acetate and the organic layers were combined and dried over anhydrous magnesium sulfate. After the solvent was removed by means of rotary evaporation, intermediate 1 was isolated by column chromatography.

The intermediate 1 was then reacted with the corresponding aromatic aldehyde to form o-aryl substituted chalcone derivatives by aldol reaction. 5-formyl-2-methoxybenzene boronic acid (180 mg, 1 mmol) and intermediate 1 (257 mg, 1.2 mmol) were dissolved in absolute ethanol, and then KOH (336 mg, 6 mmol) was added. The reaction mixture was stirred at room temperature until 5-formyl-2-methoxybenzene boronic acid disappeared as monitored by TLC. The mixture was adjusted to be acid by diluted hydrochloric acid. And absolute ethanol was removed by means of rotary evaporation. The mixture was extracted with ethyl acetate, and the organic layer was dried over anhydrous magnesium sulfate and rotary evaporated. The final product compound 1 was isolated by column chromatography as a pale yellow solid, yielded 70.45%; $^1$H NMR (400 MHz, $CDCl_3$) δ 7.79 (d, J=2.3 Hz, 1H), 7.60 (d, J=7.6 Hz, 1H), 7.57-7.52 (m, 1H), 7.48-7.39 (m, 3H), 7.36-7.28 (m, 3H), 7.03 (t, J=8.7 Hz, 2H), 6.86 (d, J=8.7 Hz, 1H), 6.56 (d, J=16.0 Hz, 1H), 5.81 (s, 2H), 3.93 (s, 3H).

Example 2

Synthesis of (E)-3-(4-(dimethylamino)phenyl)-1-(4'-fluoro[1,1'-biphenyl]-2-yl) prop-2-en-1-one (compound 2)

Intermediate 1 obtained in Example 1 (257 mg, 1.2 mmol) and 4-dimethylaminobenzaldehyde (149 mg, 1 mmol) were dissolved in absolute ethanol, followed by addition of KOH (336 mg, 6 mmol). The reaction mixture was stirred at room temperature until 4-dimethylaminobenzaldehyde disappeared as monitored by TLC. The ethanol was removed by means of rotary evaporation. The mixture was extracted with ethyl acetate, and the organic layer was dried over by anhydrous magnesium sulfate and rotary evaporated. The compound 2 was isolated by column chromatography as a yellow solid, yielded 67.26%; $^1$H NMR (400 MHz, DMSO) δ 7.61-7.56 (m, 1H), 7.54-7.49 (m, 2H), 7.46 (d, J=7.6 Hz, 1H), 7.39-7.30 (m, 4H), 7.23-7.14 (m, 3H), 6.64 (d, J=8.8 Hz, 2H), 6.53 (d, J=15.9 Hz, 1H), 2.96 (s, 6H).

Example 3

Synthesis of (E)-1-(3'-fluoro[1,1'-biphenyl]-2-yl)-3-(3-hydroxy-4-methoxyphenyl) prop-2-en-1-one (compound 3)

A biphenyl intermediate 1-(3'-fluoro-[1,1'-biphenyl]-2-yl) ethanone (intermediate 2) was obtained by Suzuki-Miyaura reaction. To a microwave reaction vial were added 1-(2-bromophenyl) ethanone (199 mg, 1.0 mmol), (3-fluorophenyl) boronic acid (182 mg, 1.3 mmol), [1,1'-bis(diphenylphosphino) ferrocene]palladium dichloride dichloromethane complex (DPPF) (50 mg, 0.06 mmol), 2M (aq) $K_2CO_3$ (1.5 ml), and 1,4-dioxane (1.5 ml). The reaction mixture was sealed and heated at 150° C. for 30 min. After the reaction was cooled, water (10 mL) was added. The mixture was extracted three times with ethyl acetate and the organic layers were combined and dried over anhydrous magnesium sulfate. After the solvent was removed by means of rotary evaporation, intermediate 2 was isolated by column chromatography.

The intermediate 2 was then reacted with the corresponding aromatic aldehyde to obtain the o-aryl substituted chalcone derivatives by aldol reaction. 3-hydroxy-4-Methoxybenzaldehyde (152 mg, 1 mmol) and intermediate 2 (257 mg, 1.2 mmol) were dissolved in absolute ethanol, followed by addition of KOH (336 mg, 6 mmol). The reaction mixture was stirred at room temperature until 3-hydroxy-4-methoxybenzaldehyde disappeared as monitored by TLC. The mixture was adjusted to be acid by diluted hydrochloric acid. And ethanol was removed by rotary evaporation. The mixture was extracted with ethyl acetate, and the organic layer was dried over anhydrous magnesium sulfate and rotary evaporated. The compound 3 was isolated by column chromatography as a yellow solid, yielded 72.38%; $^1$H NMR (400 MHz, $CDCl_3$) δ 7.61 (d, J=7.5 Hz, 1H), 7.54 (dd, J=7.5, 1.2 Hz, 1H), 7.48 (dd, J=7.4, 1.0 Hz, 1H), 7.44 (d, J=7.7 Hz, 1H), 7.33-7.29 (m, 1H), 7.26 (d, J=15.9 Hz, 1H), 7.15-7.11 (m, 1H), 7.09 (d, J=9.7 Hz, 1H), 6.98 (td, J=8.5, 1.5 Hz, 1H), 6.88 (s, 1H), 6.84 (d, J=8.3 Hz, 1H), 6.77 (d, J=8.3 Hz, 1H), 6.50 (d, J=15.9 Hz, 1H), 5.65 (s, 1H), 3.89 (s, 3H).

Example 4

Synthesis of (E)-3-(3-hydroxy-4-methoxyphenyl)-1-(3',4',5'-trimethoxy[1,1'-biphenyl]-2-yl)prop-2-en-1-one (compound 4)

A biphenyl intermediate 1-(3',4',5'-trimethoxy[1,1'-biphenyl]-2-yl) ethanone (intermediate 3) was obtained by Suzuki-Miyaura reaction. To a microwave reaction vial were added 1-(2-bromophenyl) ethanone (199 mg, 1.0 mmol), (3,4,5-trimethoxyphenyl) boronic acid (275.6 mg, 1.3 mmol), [1,1'-bis(diphenylphosphino) ferrocene]palladium dichloride dichloromethane complex (DPPF) (50 mg, 0.06 mmol), 2M (aq) $K_2CO_3$ (1.5 ml), and 1,4-dioxane (1.5 ml). The reaction mixture was sealed and heated at 150° C. for 30 min. After the reaction was cooled, water (10 mL) was added. The mixture was extracted three times with ethyl acetate and the organic layers were combined and dried over anhydrous magnesium sulfate. After the solvent was removed by rotary evaporation, intermediate 3 was isolated by column chromatography.

The intermediate 3 was then reacted with the corresponding aromatic aldehyde to obtain the o-aryl substituted chalcone derivatives by aldol reaction. 3-hydroxy-4-methoxybenzaldehyde (152 mg, 1 mmol) and intermediate 3 (343 mg, 1.2 mmol) were dissolved in absolute ethanol, followed by addition of KOH (336 mg, 6 mmol). The reaction mixture was stirred at room temperature until 3-hydroxy-4-methoxybenzaldehyde disappeared as monitored by TLC. The mixture was adjusted to be acid by diluted hydrochloric acid. The ethanol was removed by means of rotary evaporation. The mixture was extracted with ethyl acetate, and the organic layer was dried over anhydrous magnesium sulfate and rotary evaporated. The compound 4 was isolated by column chromatography as a yellow oil, yielded 79.14%; $^1$H NMR (400 MHz, CDCl$_3$) δ 7.61 (d, J=7.6 Hz, 1H), 7.56-7.51 (m, 1H), 7.50-7.41 (m, 2H), 7.26 (d, J=15.4 Hz, 1H), 6.84-6.77 (m, 2H), 6.74 (d, J=8.3 Hz, 1H), 6.59 (s, 2H), 6.45 (d, J=15.4 Hz, 1H), 5.66 (s, 1H), 3.87 (s, 3H), 3.80 (s, 6H), 3.77 (d, J=0.5 Hz, 3H).

Example 5

Synthesis of (E)-3-(3-hydroxy-4-methoxyphenyl)-1-(2',3',4'-trimethoxy[1,1'-biphenyl]-2-yl) prop-2-en-1-one (compound 5)

A biphenyl intermediate 1-(2',3',4'-trimethoxy[1,1'-biphenyl]-2-yl) ethanone (intermediate 4) was obtained by Suzuki-Miyaura reaction. To a microwave reaction vial were added 1-(2-bromophenyl) ethanone (199 mg, 1.0 mmol), (2,3,4-trimethoxyphenyl) boronic acid (275.6 mg, 1.3 mmol), [1,1'-bis(diphenylphosphino) ferrocene]palladium dichloride dichloromethane complex (DPPF) (50 mg, 0.06 mmol), 2M (aq) K$_2$CO$_3$ (1.5 ml), and 1,4-dioxane (1.5 ml). The reaction mixture was sealed and heated at 150° C. for 30 min. After the reaction was cooled, water (10 mL) was added. The mixture was extracted three times with ethyl acetate and the organic layers were combined and dried over anhydrous magnesium sulfate. After the solvent was removed by rotary evaporation, intermediate 4 was isolated by column chromatography.

The intermediate 4 was then reacted with the corresponding aromatic aldehyde to obtain the o-aryl substituted chalcone derivatives by aldol reaction. 3-hydroxy-4-methoxybenzaldehyde (152 mg, 1 mmol) and intermediate 4 (343 mg, 1.2 mmol) were dissolved in absolute ethanol, and then KOH (336 mg, 6 mmol) was added. The reaction mixture was stirred at room temperature until 3-hydroxy-4-methoxybenzaldehyde disappeared as monitored by TLC. The mixture was adjusted to be acid by diluted hydrochloric acid. The ethanol was removed by means of rotary evaporation. The mixture was extracted with ethyl acetate, and the organic layer was dried over anhydrous magnesium sulfate and rotary evaporated. The final product compound 5 was isolated by column chromatography as a yellow solid, yielded 62.75%; $^1$H NMR (400 MHz, DMSO) δ 9.11 (s, 1H), 7.63-7.55 (m, 2H), 7.47 (td, J=7.5, 1.1 Hz, 1H), 7.38 (d, J=7.6 Hz, 1H), 7.23 (d, J=15.8 Hz, 1H), 6.94-6.81 (m, 5H), 6.51 (d, J=15.8 Hz, 1H), 3.78 (s, 3H), 3.77 (s, 3H), 3.55 (s, 3H), 3.50 (s, 3H).

Example 6

Synthesis of (E)-(5-(3-(3'-fluoro[1,1'-biphenyl]-2-yl)-3-oxoprop-1-en-1-yl)-2-methoxyphenyl) boronic acid (compound 6)

5-formyl-2-methoxybenzene boronic acid (180 mg, 1 mmol) and intermediate 2 obtained in Example 3 (257 mg, 1.2 mmol) were dissolved in absolute ethanol, and then KOH (336 mg, 6 mmol) was added. The reaction mixture was stirred at room temperature until 5-formyl-2-methoxybenzene boronic acid disappeared as monitored by TLC. The mixture was adjusted to be acid by diluted hydrochloric acid. The ethanol was removed by means of rotary evaporation. The mixture was extracted with ethyl acetate, and the organic layer was dried over anhydrous magnesium sulfate and rotary evaporated. The final product compound 6 was isolated by column chromatography as a pale yellow solid, yielded 61.51%; $^1$H NMR (400 MHz, CDCl$_3$) δ 7.61 (d, J=7.8 Hz, 1H), 7.55 (d, J=6.9 Hz, 1H), 7.46 (m, 2H), 7.16-7.07 (m, 3H), 6.99 (dd, J=16.0, 8.0 Hz, 2H), 6.84 (d, J=8.6 Hz, 2H), 6.68 (d, J=8.6 Hz, 1H), 6.59 (d, J=15.9 Hz, 1H), 5.71 (s, 2H), 3.86 (s, 3H).

Example 7

Synthesis of (E)-3-(4-(dimethylamino)phenyl)-1-(3'-fluoro[1,1'-biphenyl]-2-yl) prop-2-en-1-one (compound 7)

4-dimethylaminobenzaldehyde (149 mg, 1 mmol) and intermediate 2 obtained in Example 3 (257 mg, 1.2 mmol) were dissolved in absolute ethanol, and then KOH (336 mg, 6 mmol) was added. The reaction mixture was stirred at room temperature until 4-dimethylaminobenzaldehyde disappeared as monitored by TLC. Ethanol was removed by rotary evaporation and the mixture was extracted with ethyl acetate. The organic layer was dried over anhydrous magnesium sulfate and rotary evaporated. The final product compound 7 was isolated by column chromatography as a yellow solid, yielded 44.35%; $^1$H NMR (400 MHz, DMSO) δ 7.59 (d, J=7.0 Hz, 1H), 7.55-7.51 (m, 2H), 7.49 (d, J=7.5 Hz, 1H), 7.42-7.38 (m, 1H), 7.34 (d, J=8.8 Hz, 2H), 7.18 (d, J=15.8 Hz, 2H), 7.13 (d, J=6.5 Hz, 2H), 6.64 (d, J=8.7 Hz, 2H), 6.57 (d, J=15.9 Hz, 1H), 2.95 (s, 6H).

Example 8

Synthesis of (E)-5-(3-(2',3',4'-trimethoxy[1,1'-biphenyl]-2-yl)-3-oxoprop-1-en-1-yl))-2-methoxyphenyl) boronic acid (compound 8)

5-formyl-2-methoxybenzene boronic acid (180 mg, 1 mmol) and intermediate 4 obtained in Example 5 (343 mg, 1.2 mmol) were dissolved in absolute ethanol, and then KOH (336 mg, 6 mmol) was added. The reaction mixture was stirred at room temperature until 5-formyl-2-methoxybenzene boronic acid disappeared as monitored by TLC. The mixture was adjusted to be acid by diluted hydrochloric acid. Ethanol was removed by rotary evaporation and the mixture was extracted with ethyl acetate. The organic layer was dried over anhydrous magnesium sulfate and rotary evaporated. The final product compound 8 was isolated by column chromatography as a pale yellow solid, yielded 49.27%; $^1$H NMR (400 MHz, DMSO) δ 7.77 (s, 2H), 7.64-7.54 (m, 3H), 7.51-7.44 (m, 2H), 7.38 (d, J=7.5 Hz, 1H), 7.29 (d, J=15.9 Hz, 1H), 6.94 (d, J=8.7 Hz, 1H), 6.91 (d, J=8.6 Hz, 1H), 6.82 (d, J=8.6 Hz, 1H), 6.61 (d, J=15.9 Hz, 1H), 3.80 (s, 3H), 3.76 (s, 3H), 3.54 (s, 3H), 3.49 (s, 3H).

Example 9

Synthesis of (E)-1-(2',3',4'-trimethoxy[1,1'-biphenyl]-2-yl)-3-(4-(dimethylamino)phenyl)prop-2-en-1-one (compound 9)

4-dimethylaminobenzaldehyde (149 mg, 1 mmol) and intermediate 4 obtained in Example 5 (343 mg, 1.2 mmol)

were dissolved in absolute ethanol, and then KOH (336 mg, 6 mmol) was added. The reaction mixture was stirred at room temperature until 4-dimethylaminobenzaldehyde disappeared as monitored by TLC. Ethanol was removed by rotary evaporation and the mixture was extracted with ethyl acetate. The organic layer was dried over anhydrous magnesium sulfate and rotary evaporated. The final product compound 9 was isolated by column chromatography as a red solid, yielded 38.63%; $^1$H NMR (400 MHz, DMSO) δ 7.57 (d, J=7.4 Hz, 1H), 7.55 (dd, J=7.0, 5.2 Hz, 1H), 7.45 (dd, J=7.5 Hz, 7.5 Hz, 1H), 7.36 (d, J=7.5 Hz, 1H), 7.25 (d, J=7.1 Hz, 2H), 7.23 (d, J=10.5 Hz, 1H), 6.88 (d, J=8.5 Hz, 1H), 6.82 (d, J=8.6 Hz, 1H), 6.62 (d, J=7.4 Hz, 2H), 6.48 (d, J=15.7 Hz, 1H), 3.77 (s, 3H), 3.56 (s, 3H), 3.51 (s, 3H), 2.95 (s, 6H).

Example 10

Synthesis of (E)-(5-(3-(3'-fluoro[1,1'-biphenyl]-2-yl)-3-oxoprop-1-en-1-yl)-2-methoxyphenol)phosphate ester (compound 10)

Phosphate esterification was performed using (E)-1-(3'-fluoro[1,1'-biphenyl]-2-yl)-3-(3-hydroxy-4-methoxyphenyl)prop-2-en-1-one (compound 3) obtained in Example 3 as a starting material, followed by removing the alkyl from the phosphate ester. Weighed chalcone (348 mg, 1 mmol) was placed in a 50 mL flask and was dissolved in CHCl$_3$. Triethylamine (Et$_3$N, 202 mg, 2 mmol) was added and the flask was placed in an ice bath. Diethyl phosphite (552 mg, 4 mmol) was dissolved in CCl$_4$ (2.0 mL) which was then mixed and placed in a dropping funnel to be added to the flask dropwise. The reaction was preformed in an ice-cold bath until the starting material disappeared as monitored by TLC. The solvent was removed by rotary evaporation, and phosphate esterified intermediate was isolated by column chromatography. This intermediate (484 mg, 1 mmol) was dissolved in CH$_2$Cl$_2$ and then added with TMSBr (3.0 g) to react at room temperature to remove ethyl group. CH$_2$Cl$_2$ was removed by rotary evaporation. MeOH (15 mL) was added and the mixture was heated in reflux for 2 h. Methanol was removed by rotary evaporated to obtain raw product. Finally, the final product compound 10 was isolated by column chromatography as a yellow-brown solid, yielded 59.21%; $^1$H NMR (400 MHz, DMSO) δ 7.66-7.60 (m, 1H), 7.53 (dd, J=15.3, 8.1 Hz, 3H), 7.43 (s, 1H), 7.40 (d, J=7.5 Hz, 1H), 7.31 (d, J=8.5 Hz, 1H), 7.20 (d, J=16.1 Hz, 1H), 7.15-7.12 (d, J=8.5 Hz, 3H), 7.05 (d, J=8.5 Hz, 1H), 6.66 (d, J=16.0 Hz, 1H), 3.83-3.78 (s, 3H).

Example 11

Synthesis of (E)-(5-(3-(4'-fluoro[1,1'-biphenyl]-2-yl)-3-oxoprop-1-en-1-yl)-2-methoxyphenol)phosphate ester (compound 11)

3-hydroxy-4-methoxybenzaldehyde (152 mg, 1 mmol) and intermediate 1 obtained in Example 1 (257 mg, 1.2 mmol) were dissolved in absolute ethanol, and then KOH (336 mg, 6 mmol) was added. The reaction mixture was stirred at room temperature until 3-hydroxy-4-methoxybenzaldehyde disappeared as monitored by TLC. The mixture was adjusted to be acid by diluted hydrochloric acid. Absolute ethanol was removed by rotary evaporation and the mixture was extracted with ethyl acetate. The organic layer was dried over anhydrous magnesium sulfate and rotary evaporated. The (E)-5-(3-(4'-fluoro[1,1'-biphenyl]-2-yl)-3-oxoprop-1-en-1-yl)-2-methoxyphenol was isolated by column chromatography.

Weighed (E)-5-(3-(4'-fluoro[1,1'-biphenyl]-2-yl)-3-oxoprop-1-en-1-yl)-2-methoxyphenol (348 mg, 1 mmol) was placed in a 50 mL flask and was dissolved in CHCl$_3$. Et$_3$N (202 mg, 2 mmol) was added and the flask was placed in an ice bath. Diethyl phosphite (552 mg, 4 mmol) was dissolved in CCl$_4$ (2.0 mL) which was then mixed and placed in a dropping funnel to be added to the flask dropwise. The reaction was performed in an ice-cold bath until the starting material disappeared as monitored by TLC. The solvent was removed by rotary evaporation, and phosphate esterified intermediate was isolated by column chromatography.

The intermediate (484 mg, 1 mmol) was dissolved in CH$_2$Cl$_2$ and then added with TMSBr (3.0 g) to react at room temperature to remove ethyl group. CH$_2$Cl$_2$ was removed by rotary evaporation. MeOH (15 mL) was added and the mixture was heated in reflux for 2 h. Methanol was removed by rotary evaporated to obtain raw product. Finally, the final product compound 11 was isolated by column chromatography as a yellow solid, yielded 40.46%; $^1$H NMR (400 MHz, DMSO) δ 7.61 (d, J=7.2 Hz, 1H), 7.55 (dd, J=11.6, 7.2 Hz, 2H), 7.49 (d, J=7.5 Hz, 1H), 7.34 (m, 3H), 7.24-7.20 (m, 3H), 7.18 (d, J=3.6 Hz, 1H), 7.06 (d, J=8.6 Hz, 1H), 6.63 (d, J=16.0 Hz, 1H), 3.81 (s, 3H).

Example 12

Synthesis of (E)-1-(3'-fluoro[1,1'-biphenyl]-2-yl)-3-(3-hydroxy) prop-2-en-1-one (compound 12)

3-hydroxybenzaldehyde (122 mg, 1 mmol) and intermediate 2 obtained in Example 3 (257 mg, 1.2 mmol) were dissolved in absolute ethanol, and then KOH (336 mg, 6 mmol) was added. The reaction mixture was stirred at room temperature until 3-hydroxybenzaldehyde disappeared as monitored by TLC. The mixture was adjusted to pH 6 by 1M of hydrochloric acid. Absolute ethanol was removed by rotary evaporation and the mixture was extracted with ethyl acetate. The organic layer was dried over anhydrous magnesium sulfate and rotary evaporated. The final product compound 12 was isolated by column chromatography as a pale yellow oil, yielded 69.3%; $^1$H NMR (400 MHz, DMSO) δ 9.57 (m, J=30.9 Hz, 1H), 7.64 (dd, J=7.3, 1.5 Hz, 1H), 7.61 (dd, J=3.5, 1.5 Hz, 1H), 7.57-7.53 (m, 1H), 7.51 (d, J=7.6 Hz, 1H), 7.42 (d, J=7.8 Hz, 1H), 7.38 (d, J=7.6 Hz, 1H), 7.23 (s, 1H), 7.20 (d, J=5.3 Hz, 1H), 7.18 (d, J=6.6 Hz, 1H), 7.14 (d, J=7.6 Hz, 1H), 7.11 (d, J=6.3 Hz, 1H), 6.92 (d, J=7.5 Hz, 1H), 6.85 (d, J=1.6 Hz, 1H), 6.71 (d, J=16.1 Hz, 1H).

Example 13

Synthesis of (E)-1-(3'-fluoro[1,1'-biphenyl]-2-yl)-3-(3-hydroxy-4-(dimethylamino)phenyl) prop-2-en-1-one (compound 13) and (E)-1-(3'-fluoro[1,1'-biphenyl]-2-yl)-3-(3-bromo-4-(dimethylamino)phenyl) prop-2-en-1-one (compound 15)

3-bromo-4-(dimethylamino)benzaldehyde (228 mg, 1 mmol) and intermediate 2 obtained in Example 3 (257 mg, 1.2 mmol) were dissolved in absolute ethanol, and then KOH (336 mg, 6 mmol) was added. The reaction mixture was stirred at room temperature until 3-bromo-4-(dimethylamino)benzaldehyde disappeared as monitored by TLC. The mixture was adjusted to be neutral by 1M of hydrochloric acid. The absolute ethanol was removed by means of rotary evaporation. The mixture was extracted with ethyl acetate, and the organic layer was dried over anhydrous magnesium sulfate and rotary evaporated. The compound 15 was isolated by column chromatography as a yellow oil, yielded 69.3%; $^1$H NMR (400 MHz, DMSO) δ 7.76 (dd, J=8.4, 7.7 Hz, 1H), 7.64 (dd, J=7.5, 1.2 Hz, 1H), 7.58 (dd, J=7.5, 1.5 Hz, 1H), 7.54-7.49 (m, 2H), 7.52 (dd, J=7.5, 1.3 Hz, 1H), 7.42 (dd, J=7.6, 0.9 Hz, 1H), 7.37-7.31 (m, 2H), 7.34 (d, J=16.0 Hz, 1H), 6.90 (dd, J=8.4, 3.0 Hz, 1H), 6.88 (m, 1H), 6.64 (d, J=16.0 Hz, 1H), 2.96 (s, 6H).

Compound 15 (425 mg, 1 mmol) was placed in a reaction flask, followed by addition of 10 ml of mixed solvent (PEG:H$_2$O=4:1), which was then stirred for 5 min. CuI (20 mg, 0.1 mmol) and KOH (536 mg, 6 mmol) was rapidly successively added. The mixture was heated at 120° C. in reflux for 8 h. After the reaction was cooled, the mixture was adjusted to pH=7 by addition of diluted hydrochloric acid. The mixture was extracted three times with ethyl acetate and the organic layers were combined and dried over anhydrous magnesium sulfate. The solvent was removed by rotary evaporation. The final product compound 13 was isolated by column chromatography as a brown-red solid, yielded 37.8%; $^1$H NMR (400 MHz, CDCl$_3$) δ 9.32 (m, J=20.9 Hz, 1H) 7.52 (dd, J=7.5, 0.9 Hz, 1H), 7.45 (td, J=7.5, 1.4 Hz, 1H), 7.39 (dd, J=7.5, 1.2 Hz, 1H), 7.35 (d, J=7.4 Hz, 1H), 7.26-7.21 (m, 1H), 7.19 (dt, J=4.6, 3.2 Hz, 1H), 7.15 (d, J=8.8 Hz, 1H), 7.06 (t, J=7.5 Hz, 1H), 7.06-7.02 (m, 2H), 6.89 (td, J=8.5, 2.1 Hz, 1H), 6.52 (d, J=8.8 Hz, 1H), 6.41 (d, J=15.8 Hz, 1H), 2.92 (s, 6H).

Example 14

Synthesis of (E)-1-(3'-fluoro[1,1'-biphenyl]-2-yl)-3-(4-cyanophenyl)prop-2-en-1-one (compound 14)

4-cyano-benzaldehyde (132 mg, 1 mmol) and intermediate 2 obtained in Example 3 (257 mg, 1.2 mmol) were dissolved in absolute ethanol, and then KOH (336 mg, 6 mmol) was added. The reaction mixture was stirred at room temperature until 4-cyano-benzaldehyde disappeared as monitored by TLC. The mixture was adjusted to be neutral by 1M of hydrochloric acid. The absolute ethanol was removed by rotary evaporation and the mixture was extracted with ethyl acetate. The organic layer was dried over anhydrous magnesium sulfate and rotary evaporated. The final product compound 14 was isolated by column chromatography as a brown-yellow solid, yielded 56.1%; $^1$H NMR (400 MHz, DMSO) δ 7.62 (dd, J=7.5, 1.4 Hz, 1H), 7.56 (td, J=7.5, 1.5 Hz, 1H), 7.48 (dd, J=7.5, 1.3 Hz, 1H), 7.44 (d, J=7.5 Hz, 1H), 7.34-7.28 (m, 1H), 7.31 (d, J=15.9 Hz, 1H), 7.24-7.27 (m, 2H), 7.15-7.08 (m, 2H), 6.98 (ddd, J=10.1, 7.7, 2.2 Hz, 1H), 6.86-6.80 (m, 2H), 6.52 (d, J=15.9 Hz, 1H).

Example 15

Synthesis of (E)-1-(3'-fluoro[1,1'-biphenyl]-2-yl)-3-(4-pyrrolidine-1-yl)prop-2-en-1-one (compound 16)

4-(pyrrolidin-1-yl)benzaldehyde (175 mg, 1 mmol) and intermediate 2 obtained in Example 3 (257 mg, 1.2 mmol) were dissolved in absolute ethanol, and then KOH (336 mg, 6 mmol) was added. The reaction mixture was stirred at room temperature until 4-(pyrrolidin-1-yl)benzaldehyde disappeared as monitored by TLC. The mixture was adjusted to be neutral by 1M of hydrochloric acid. The absolute ethanol was removed by rotary evaporation and the mixture was extracted with ethyl acetate. The organic layer was dried over anhydrous magnesium sulfate and rotary evaporated. The final product compound 16 was isolated by recrystallization with ethanol as a dark purple crystal, yielded 67%; $^1$H NMR (400 MHz, CDCl3) δ 7.61 (d, J=7.3 Hz, 1H), 7.53 (d, J=7.4 Hz, 1H), 7.49-7.46 (m, 1H), 7.44 (d, J=7.3 Hz, 1H), 7.36-7.31 (m, 2H), 7.29 (d, J=7.3 Hz, 1H), 7.23 (d, J=8.6 Hz, 1H), 7.17 (d, J=8.4 Hz, 1H), 7.14 (d, J=7.8 Hz, 1H), 6.98 (dd, J=11.5, 4.8 Hz, 1H), 6.50 (d, J=12.1 Hz, 1H), 6.46 (m, 2H), 3.31 (s, 4H), 2.38-1.56 (m, 4H).

Example 16

Synthesis of (E)-1-(3'-Fluoro[1,1'-biphenyl]-2-yl)-3-(4-(diphenylamino)phenyl)prop-2-en-1-one (compound 17)

4-N,N-diphenyl-benzaldehyde (274 mg, 1 mmol) and intermediate 2 obtained in Example 3 (257 mg, 1.2 mmol) were dissolved in absolute ethanol, and then KOH (336 mg, 6 mmol) was added. The reaction mixture was stirred at room temperature until 4-N,N-diphenyl-benzaldehyde disappeared as monitored by TLC. The mixture was adjusted to be neutral by 1M of hydrochloric acid. The absolute ethanol was removed by rotary evaporation and the mixture was extracted with ethyl acetate. The organic layer was dried over anhydrous magnesium sulfate and rotary evaporated. The final product compound 17 was isolated by column chromatography as a yellow orange solid, yielded 80.1%; $^1$H NMR (400 MHz, CDCl3) δ 7.53 (d, J=7.4 Hz, 1H), 7.50-7.43 (m, 2H), 7.39 (t, J=5.9 Hz, 1H), 7.36 (d, J=7.7 Hz, 1H), 7.25-7.22 (m, 2H), 7.20 (dd, J=11.8, 4.4 Hz, 4H), 7.10-7.05 (m, 3H), 7.02 (t, J=7.5 Hz, 5H), 6.92 (t, J=8.4 Hz, 1H), 6.83 (m, 2H), 6.43 (d, J=15.9 Hz, 1H).

Example 17

Synthesis of (E)-4-(3'-fluoro[1,1'-biphenyl]-2-yl)-3-oxoprop-1-en-1-yl benzoic acid (compound 18)

4-formyl-benzoic acid (150 mg, 1 mmol) and intermediate 2 obtained in Example 3 (257 mg, 1.2 mmol) were dissolved in absolute ethanol, and then KOH (772 mg, 12 mmol) was added. The reaction mixture was stirred at room temperature until 4-formyl-benzoic acid disappeared as monitored by TLC. The mixture was adjusted to pH=4 by 1M of hydrochloric acid. The absolute ethanol was removed by rotary evaporation and the mixture was extracted with ethyl acetate. The organic layer was dried over anhydrous magnesium sulfate and rotary evaporated. The final product compound 18 was isolated by column chromatography as a pale yellow solid, yielded 67.3%; $^1$H NMR (400 MHz, DMSO) δ 13.07 (s, 1H), 7.89 (d, J=8.2 Hz, 1H), 7.67 (dd, J=9.2, 4.6 Hz, 1H), 7.66-7.62 (m, 2H), 7.58 (d, J=7.2 Hz, 1H), 7.54 (d, J=7.7 Hz, 1H), 7.45-7.40 (m, 2H), 7.38 (s, 1H), 7.36 (d, J=16.1 Hz, 1H), 7.22-7.17 (m, 2H), 7.16 (dd, J=14.4, 6.5 Hz, 1H), 6.96 (d, J=16.1 Hz, 1H).

Example 18

Synthesis of (E)-1-(3'-fluoro[1,1'-biphenyl]-2-yl)-3-(3-aminophenyl)prop-2-en-1-one (compound 19)

3-amino-benzaldehyde (121 mg, 1 mmol) and intermediate 2 obtained in Example 3 (257 mg, 1.2 mmol) were dissolved with absolute ethanol, and then KOH (336 mg, 6 mmol) was added. The reaction mixture was stirred at room temperature until 3-amino-benzaldehyde disappeared as monitored by TLC. The mixture was adjusted to be neutral by 1M of hydrochloric acid. The absolute ethanol was removed by rotary evaporation and the mixture was extracted with ethyl acetate. The organic layer was dried over anhydrous magnesium sulfate and rotary evaporated. The final product compound 19 was isolated by column chromatography as a yellow solid, yielded 48.7%; $^1$H NMR (400 MHz, DMSO) δ 7.72 (dd, J=7.3, 1.5 Hz, 1H), 7.68 (dd, J=3.5, 1.5 Hz, 1H), 7.65 (d, J=7.6 Hz, 1H), 7.64-7.62 (m, 2H), 7.56 (d, J=7.8 Hz, 1H), 7.38 (d, J=7.6 Hz, 1H), 7.28 (d, J=5.3 Hz, 1H), 7.18 (d, J=6.6 Hz, 1H), 7.14 (d, J=7.6 Hz, 1H), 7.11 (d, J=6.3 Hz, 1H), 6.92 (d, J=7.5 Hz, 1H), 6.75 (d, J=1.6 Hz, 1H), 6.63 (d, J=16.1 Hz, 1H), 4.26 (s, 2H).

Example 19

Synthesis of (E)-3-(3'-fluoro[1,1'-biphenyl]-2-yl)-3-oxoprop-1-en-1-yl benzoic acid (compound 20)

3-formyl-benzoic acid (150 mg, 1 mmol) and intermediate 2 obtained in Example 3 (257 mg, 1.2 mmol) were dissolved in absolute ethanol, and then KOH (772 mg, 12 mmol) was added. The reaction mixture was stirred at room temperature until 3-formyl-benzoic acid disappeared as monitored by TLC. The mixture was adjusted to pH=4 by 1M of hydrochloric acid. The absolute ethanol was removed by rotary evaporation and the mixture was extracted with ethyl acetate. The organic layer was dried over anhydrous magnesium sulfate and rotary evaporated. The final product compound 20 was isolated by column chromatography as a yellow solid, yielded 61.2%; $^1$H NMR (400 MHz, CDCl$_3$), δ 13.14 (s, 1H), 8.01 (d, J=10.8 Hz, 1H), 7.89 (dd, J=9.2, 4.6 Hz, 1H), 7.78 (d, J=7.2 Hz, 1H), 7.73-7.69 (m, 2H), 7.64 (dd, J=7.7, 5.3 Hz, 1H), 7.58 (d, J=9.8 Hz, 1H), 7.54 (s, 1H), 7.48-7.41 (m, 2H), 7.36 (d, J=16.1 Hz, 1H), 7.22 (s, 1H), 7.16 (d, J=15.1 Hz, 1H), 6.87 (d, J=15.4 Hz, 1H).

Example 20

Synthesis of (E)-5-(3-(3'-fluoro[1,1'-biphenyl]-2-yl)-3-oxoprop-1-en-1-yl)-2-hydroxybenzenesulfonic acid (compound 21)

5-formyl-2-hydroxy benzene sulfonic acid (202 mg, 1 mmol) and intermediate 2 obtained in Example 3 (257 mg, 1.2 mmol) were dissolved in absolute ethanol, and then KOH (336 mg, 6 mmol) was added. The reaction mixture was heated at 85° C. in reflux for 16 h until 3-hydroxy benzaldehyde disappeared as monitored by TLC. The mixture was adjusted to pH=6 by 1M of hydrochloric acid. The absolute ethanol was removed by rotary evaporation and the mixture was extracted with ethyl acetate. The organic layer was dried over anhydrous magnesium sulfate and rotary evaporated. The final product compound 21 was isolated by column chromatography as a yellow solid, yielded 51.54%; $^1$H NMR (400 MHz, Acetone) δ 7.86 (s, 1H), 7.63-7.55 (m, 2H), 7.49 (t, J=7.4 Hz, 2H), 7.39-7.35 (m, 2H), 7.23 (d, J=16.1 Hz, 1H), 7.17 (d, J=7.7 Hz, 1H), 7.11 (d, J=10.0 Hz, 1H), 7.05 (dd, J=11.8, 5.2 Hz, 1H), 6.82 (d, J=8.4 Hz, 1H), 6.68 (d, J=16.4 Hz, 1H), 5.23 (s, 1H).

Example 21

Synthesis of (E)-5-(3-(4'-fluoro[1,1'-biphenyl]-2-yl)-3-oxoprop-1-en-1-yl)-2-hydroxybenzenesulfonic acid (compound 22)

5-formyl-2-hydroxy benzene sulfonic acid (202 mg, 1 mmol) and intermediate 1 obtained in Example 1 (257 mg, 1.2 mmol) were dissolved in absolute ethanol, and then KOH (336 mg, 6 mmol) was added. The reaction mixture was heated at 85° C. in reflux for 16 h until 3-hydroxy benzaldehyde disappeared as monitored by TLC. The mixture was adjusted to pH=6 by 1M of hydrochloric acid. The absolute ethanol was removed by rotary evaporation and the mixture was extracted with ethyl acetate. The organic layer was dried over anhydrous magnesium sulfate and rotary evaporated. The final product compound 22 was isolated by column chromatography as a yellow solid, yielded 53.44%; $^1$H NMR (400 MHz, DMSO) δ 11.11 (s, 1H), 7.61 (dd, J=13.7, 6.3 Hz, 1H), 7.57 (t, J=6.7 Hz, 1H), 7.52 (d, J=7.2 Hz, 1H), 7.48 (d, J=3.0 Hz, 1H), 7.41 (d, J=7.9 Hz, 1H), 7.38-7.34 (m, 2H), 7.33 (d, J=6.9 Hz, 1H), 7.28 (d, J=8.9 Hz, 1H), 7.23 (t, J=6.2 Hz, 1H), 7.19 (d, J=8.9 Hz, 1H), 6.74 (d, J=8.3 Hz, 1H), 6.62 (d, J=16.0 Hz, 1H).

Example 22

Synthesis of (E)-5-(3-(3'-fluoro[1,1'-biphenyl]-2-yl)-3-oxoprop-1-en-1-yl)-2-methoxy benzenesulfonic acid (compound 23)

5-formyl-2-methoxy-benzene sulfonic acid (216 mg, 1 mmol) and intermediate 2 obtained in Example 3 (257 mg, 1.2 mmol) were dissolved in absolute ethanol, and then KOH (336 mg, 6 mmol) was added. The reaction mixture was heated at 85° C. in reflux for 16 h until 3-hydroxy benzaldehyde disappeared as monitored by TLC. The mixture was adjusted to pH=6 by 1M of hydrochloric acid. The absolute ethanol was removed by rotary evaporation and the mixture was extracted with ethyl acetate. The organic layer was dried over anhydrous magnesium sulfate and rotary evaporated. The final product compound 23 was isolated by column chromatography as a yellow solid, yielded 58.74%; $^1$H NMR (400 MHz, Acetone) δ 7.72 (s, 1H), 7.59-7.51 (m, 2H), 7.45 (t, J=6.9 Hz, 2H), 7.31-7.28 (m, 2H), 7.20 (d, J=15.7 Hz, 1H), 7.14 (d, J=7.9 Hz, 1H), 7.08 (d, J=9.8 Hz, 1H), 7.04 (dd, J=10.9, 5.4 Hz, 1H), 6.81 (d, J=8.1 Hz, 1H), 6.70 (d, J=16.1 Hz, 1H), 3.87 (s, 3H).

Example 23

Synthesis of (E)-5-(3-(4'-fluoro[1,1'-biphenyl]-2-yl)-3-oxoprop-1-en-1-yl)-2-methoxy benzenesulfonic acid (compound 24)

5-formyl-2-methoxy-benzene sulfonic acid (216 mg, 1 mmol) and intermediate 1 obtained in Example 1 (257 mg, 1.2 mmol) were dissolved in absolute ethanol, and then KOH (336 mg, 6 mmol) was added. The reaction mixture was heated at 85° C. in reflux for 16 h until 3-hydroxy benzaldehyde disappeared as monitored by TLC. The mixture was adjusted to pH=6 by 1M of hydrochloric acid. The absolute ethanol was removed by rotary evaporation and the mixture was extracted with ethyl acetate. The organic layer was dried over anhydrous magnesium sulfate and rotary evaporated. The final product compound 24 was isolated by column chromatography as a yellow solid, yielded 60.47%; $^1$H NMR (400 MHz, DMSO) δ 7.59 (dd, J=13.9, 6.3 Hz, 1H), 7.55 (t, J=6.4 Hz, 1H), 7.49 (d, J=6.9 Hz, 1H), 7.44 (d, J=3.2 Hz, 1H), 7.39 (d, J=7.7 Hz, 1H), 7.34-7.29 (m, 2H), 7.30 (d, J=7.1 Hz, 1H), 7.24 (d, J=9.1 Hz, 1H), 7.19 (t, J=6.5 Hz, 1H), 7.15 (d, J=8.7 Hz, 1H), 6.71 (d, J=8.1 Hz, 1H), 6.65 (d, J=15.7 Hz, 1H), 3.91 (s, 3H).

Example 24

Anti-Proliferative Activity of o-Phenyl Chalcone Compounds Against a Panel of Tumor Cell Lines The present example evaluated the anti-tumor activity of the molecules provided by the present invention. The present example mainly used a method with SRB (sulforhodamine B) dying, in which proteins in the cell were stained with SRB dye to determine protein content in the cell so as to characterize cell growth density. Firstly, the test compound was formulated into a stock solution (10 mM), which was stored at 4° C. in a refrigerator. Prior to beginning the assay, the stock solution was diluted with DMSO into a series of different concentrations. The required concentrations were obtained by diluting with complete growth medium. Well growing cells were seeded in a 96-well plate (5000 cells/well, 100 uL) and cultured in an incubator at 37° C., 5% $CO_2$, and 90% RH. 24 h later, the prepared compound solution (100 μL) was slowly added to cell solution in the 96-well plate, and the well with DMSO (final concentration 0.5%) instead of the drug was used as a drug free control. The plate was incubated for 48 h. In addition, a day 0 plate that was drug free was directly detected after cell seeded in the plate for 24 h. The 96-well plate was taken out and added with trichloroacetic acid (50 μL, final concentration 10%). The plate was incubated at 4° C. for 1 h to fix the cells.

The plate was washed with ultrapure water and air-dried. The plate was then stained with SRB dye (0.4% in 1% acetic acid, 100 μL) for 30 min at room temperature. The plate was then washed with 1% acetic acid and then air-dried. A Tris base solution (100 μL, 10 mM, pH10.4) was added, after which the plate was gently shaken for 1 h on an orbital shaker to ensure that the dyes were completed dissolved. The optical density (OD) was recorded on a TECAN Infinite M200 Pro multimode reader at 515 nm. The cell growth (% of control)=(OD value of wells added with drug−mean OD value of Day 0 plate)/(OD value of DMSO drug-free control well−mean OD value of Day 0 plate)*100. Nonlinear regression fit to the cell growth rate was performed with a GraphPad Prism software, so as to obtain a curve of the cell growth rate verse compound concentration (% of control-concentration), and the compound concentration required to inhibit tumor cell growth by 50% (IC50) was obtained.

Human ovary cancer cells A2780, human colon cancer cells HCT8, human breast cancer cells MCF7, human lung cancer cells A549, human colon cancer cells SW480, human nasopharyngeal carcinoma cells CNE2, and human liver cancer cell HepG2 were chosen as representatives of tumors, while colchicine and doxorubicin were used as positive control molecules. The activities of the test molecules in inhibiting tumor cell growth are shown in Table 1.

TABLE 1

Anti-proliferative Activities of o-Phenyl Chalcone Compounds against seven Cancer Cell Lines $(IC_{50})^a$

| Compd | A2780 | HCT-8 | A549 | MCF-7 | CNE2 | SW480 | HepG2 |
|---|---|---|---|---|---|---|---|
| 1 | 63 | 63 | 70 | 40 | 83 | 41 | 30 |
| 2 | 94 | 133 | 64 | 66 | 36 | 47 | 58 |
| 3 | 13 | 16 | 11 | 65 | 17 | 12 | 14 |
| 4 | 69 | 56 | 69 | 82 | 37 | 61 | 46 |
| 5 | 74 | 59 | 55 | 96 | 45 | 74 | 52 |
| 6 | 62 | 54 | 59 | 83 | 55 | 55 | 37 |
| 7 | 73 | 92 | 48 | 48 | 25 | 44 | 37 |
| 8 | 98 | 118 | 64 | 114 | 86 | 74 | 78 |
| 9 | 117 | 153 | 85 | 124 | 53 | 37 | 72 |
| 10 | 59 | 61 | 10 | 51 | 30 | 9 | 10 |
| 11 | 65 | 88 | 23 | 96 | 52 | 22 | 39 |
| 12 | 39 | 36 | 44 | 87 | 55 | 48 | 44 |
| 13 | 10 | 14 | 11 | 69 | 15 | 6 | 9 |
| 14 | 122 | 102 | 88 | 128 | 61 | 43 | 65 |
| 15 | 89 | 99 | 88 | 124 | 46 | 87 | 44 |
| 16 | 106 | 123 | 86 | 106 | 36 | 52 | 71 |
| 17 | 133 | 137 | 74 | 123 | 43 | 51 | 93 |
| 18 | 47 | 68 | 65 | 116 | 33 | 47 | 23 |
| 19 | 38 | 42 | 64 | 92 | 35 | 57 | 34 |
| 20 | 35 | 28 | 45 | 79 | 21 | 49 | 29 |
| 21 | 16 | 20 | 18 | 49 | 19 | 16 | 18 |
| 22 | 39 | 35 | 38 | 70 | 23 | 19 | 20 |
| 23 | 10 | 12 | 14 | 42 | 16 | 10 | 12 |
| 24 | 15 | 17 | 20 | 55 | 18 | 14 | 13 |
| $COL^b$ | 57 | 59 | 36 | 19 | 34 | 33 | 35 |
| $DOX^c$ | 83 | 165 | 291 | 138 | 75 | 98 | 170 |

$^a IC_{50}$ = the compound concentration required to inhibit tumor cell proliferation by 50%. The experiments were repeated at least two times.
$^b$ colchicines,
$^c$ adriamycin.

As shown in Table 1, all of the test compounds show nanomolar concentration of $IC_{50}$ against all the test cell lines. The $IC_{50}$ of the majority of compounds approached or exceeded the positive molecule, indicating superior anti-tumor activity. The inhibitory effects against cell lines A2780, HCT-8, A549, MCF-7, CNE2, SW480 and HepG2 are less than 133 nM, 153 nM, 88 nM, 128 nM, 86 nM, 87 nM and 93 nM, respectively.

Example 25

Anti-Proliferative Activity of o-Phenyl Chalcone Compounds Against a Panel of Drug-Resistant Tumor Cell Lines We also evaluated the anti-proliferation activities of selected compounds against drug-resistant cancer cell lines. Paclitaxel-resistant human ovarian carcinoma cell A2780/TAX, incristine resistant human ileocecum carcinoma cell HCT-8/VCT, doxorubicin resistant breast cancer cell MCF-7/DOX, and cis-platinum resistant human lung cancer cell A549/CDDP were used in the example. Colchicine, paclitaxel, vincristine, and doxorubicin were employed as positive controls to evaluate the anti-proliferation activities. The method used here is in accordance with the SRB assay of Example 21, and the results were summarized in Table 2.

TABLE 2

Anti-proliferative activity of chalcone compounds against four drug-resistant tumor cell line $(IC_{50})^a$

| Compd | A2780/TAX | HCT-8/VCT | A549/CDDP | MCF-7/DOX |
|---|---|---|---|---|
| 1 | 227 | 84 | 74 | 24 |
| 2 | 49 | 96 | 105 | 45 |
| 3 | 190 | 57 | 121 | 2 |
| 4 | 364 | 238 | 93 | 66 |
| 5 | 289 | 266 | 122 | 59 |
| 6 | 124 | 78 | 63 | 74 |

TABLE 2-continued

Anti-proliferative activity of chalcone compounds against four drug-resistant tumor cell line (IC$_{50}$)[a]

| Compd | Cancer cell line IC$_{50}$ (nM) | | | |
|---|---|---|---|---|
| | A2780/TAX | HCT-8/VCT | A549/CDDP | MCF-7/DOX |
| 7 | 55 | 86 | 68 | 32 |
| 8 | 234 | 156 | 247 | 75 |
| 9 | 156 | 169 | 401 | 53 |
| 10 | 92 | 115 | 102 | 10 |
| 11 | 125 | 263 | 301 | 26 |
| 12 | 130 | 117 | 317 | 26 |
| 13 | 43 | 37 | 69 | 5 |
| 14 | 375 | 386 | 468 | 132 |
| 15 | 95 | 112 | 118 | 75 |
| 16 | 149 | 166 | 135 | 75 |
| 17 | 158 | 176 | 165 | 66 |
| 18 | 496 | 420 | 430 | 38 |
| 19 | 143 | 157 | 232 | 43 |
| 20 | 120 | 119 | 221 | 54 |
| 21 | 123 | 69 | 74 | 11 |
| 22 | 136 | 81 | 63 | 21 |
| 23 | 53 | 62 | 42 | 3 |
| 24 | 61 | 85 | 93 | 8 |
| COL[b] | 594 | 1125 | 81 | 3218 |
| TAX[c] | 2942 | 2600 | 9 | 7576 |
| DOX[d] | 1939 | 3417 | 290 | 14590 |
| VCT[e] | 927 | 1920 | 56 | 4252 |

[a]IC$_{50}$ = the compound concentration required to inhibit tumor cell proliferation by 50%. Data is an average from at least two independent experiments.
[b]Colchicine,
[c]paclitaxel,
[d]doxorubicin, and
[e]vincristine.

As shown in Table 2, all of the tested compounds exhibit superior inhibitory effects against the four drug-resistant tumor cell lines. The IC$_{50}$ of compounds is mostly in the nanomole concentration range. The four positive molecules were insensitive to each kind of drug-resistant tumor cell line except for A549/CDDP. The IC$_{50}$ values of tested compound are significantly higher than those of positive controls. The most potent compound is 7000 times over the inhibitory activity of positive drugs, which exhibited the superior anti-tumor activity.

Example 26

Microtubule Polymerization Inhibition Assay of o-Phenyl Chalcone Compounds

The example demonstrated that the active molecules of present invention have inhibitory abilities towards microtubule polymerization. Tubulin polymerization assay kit was used in the example, and the accompanying experimental protocol was followed. The specific method was described below.

Prior to the assay, the compounds were diluted with DMSO into a series of different concentrations and then diluted with sterile ultra-pure water into 10× solution of compounds. A 96-well plate was pre-warmed to 37° C. for 30 min in a multi-functional microplate reader. Reaction solution (2 mg/ml tubulin, 80 mM PIPES pH6.9, 2.0 mM MgCl2, 0.5 mM EGTA, 1.0 mM GTP, 15% glycerin) is prepared by materials needed in microtubule polymerization (tubulin buffer 85 uL, Glycerin buffer 150 μL, general buffer 205 μL, GTP (1 mM) 4.4 μL). 5 μL solution of compound were added into the 96-well plate and incubated in a microplate reader for 1 min. DMSO was employed as a control. The plate was taken out and then reaction solution was immediately added (50 ml per well). The plate was then immediately placed back into the reader and vibrated for 5 seconds before recording. The microplate reader was set at 37° C., and monitored in a kinetic model with emission wavelength at 450 nm and excitation wavelength at 360 nm. The plate was mixed and measured every minute and determined for 1 hour. A curve of fluorescence intensity v.s. time was obtained and the inhibition rate was calculated by the following formula. GraphPad Prism software was used to determine the IC$_{50}$.

Inhibition rate=[1−(average value of plateau of test curve−value of time 0)/(average value of plateau of DMSO curve−value of time 0)]*100.

Compounds 1-5 were selected for the assay and colchicine was employed as control to evaluate inhibitory activity. The results were summarized in Table 3.

TABLE 3

The IC$_{50}$[a] on inhibition of microtubules polymerization.

| Compd | IC$_{50}$ (μM) |
|---|---|
| 1 | 3.411 |
| 2 | 3.561 |
| 3 | 0.487 |
| 4 | 2.780 |
| 5 | 6.500 |
| Colchicine | 3.571 |

[a]IC$_{50}$ = the compound concentration required to inhibit microtubule polymerization by 50%.

As shown in Table 3, the representative molecules of the invention have significantly inhibitory ability to microtubule polymerization. The activity of these molecules is equal or better than that of the control molecule.

Example 27

Assessment of Active Molecules on Inhibiting Microtubule Re-Assembly and Interfering Mitosis on Cellular Level Compound 3 was a representative molecule in this example and proved to have the ability to inhibit the microtubule re-assembly and interfere mitosis on cellular level. The method was primarily described here below. A549 cells were seeded in a confocal culture dish at 8×10$^4$ cells/dish, grown for 24 h and divided into two groups. DMSO (0.5%) was added to one group followed by culture for 24 h. Compound 3 (31 nM) was added to the other group followed by culture for 24 h. Then cells of two dishes were fixed directly (37° C.). The remaining cells were placed in ice for 1 h, then at 37° C. for 0, 5, 10, and 15 min. Cells were then fixed with paraformaldehyde (4%) for 15 min. Then cells were subject to permeabilization buffer for 15 min. Primary β-tubulin mouse antibody was added and incubated at room temperature for 1 h. Cells were incubated with DyLight 549-conjugated goat anti-mouse IgG (secondary antibody) along with DAPI (stain nucleus) for 30 min. Photographs were obtained by Laser scanning confocal microscope.

FIG. 1 showed the effect of compound no. 3 on microtubules, microtubule re-assembly and mitosis: a, c-f, was the solvent control group (0.5% DMSO added), b, g-j was test group (31 nM compound no. 3 added), Scale bars: 10 μM.

As shown in FIG. 1, the filiform structure of microtubule was affected after the addition of compound 3 and microtubule depolymerized to form discreet tublin. However, microtubule was automatically deploymerized into an meshy state in the ice incubation system. With the temperature increasing, tublin was automatically re-assemble into microtubule in the system without compound 3 and a bipolarization of spindle phenomenon was observed in mitotic phase. The automatic polymerization was obviously inhibited in the system with compound 3 and abnormal events such as multipolarization of spindle and multinucleation were observed in mitotic phase.

The results of examples 26-27 firmly demonstrated that the active molecules of the present invention can interfere with the mitosis of tumor cells by inhibiting tubulin polymerization to obtain anti-tumor effects.

What is claimed is:

1. O-phenyl chalcone compounds, having molecular structures indicated in the following:

1

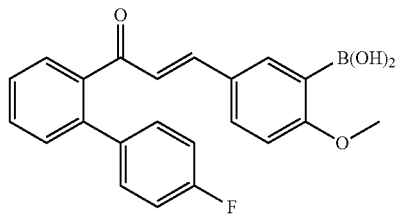

2

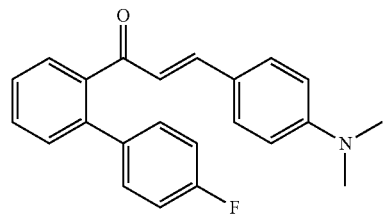

3

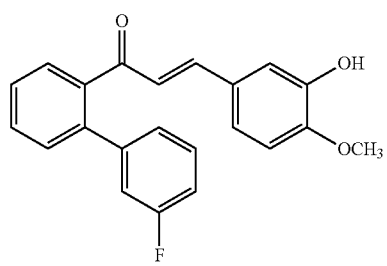

4

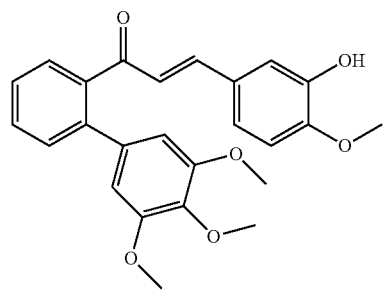

5

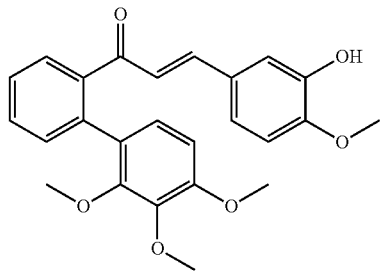

6

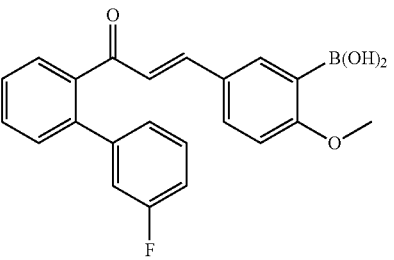

7

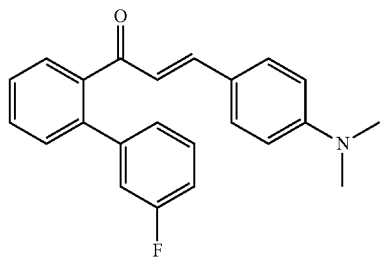

8

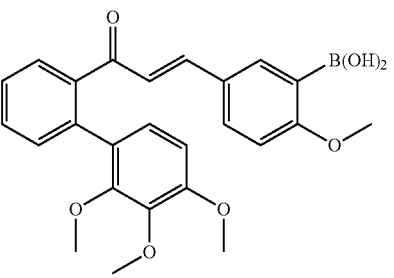

9

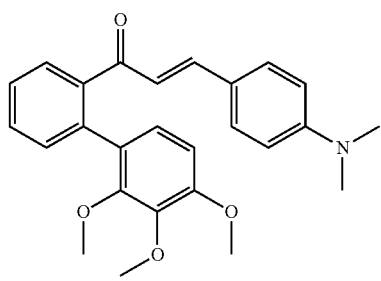

10
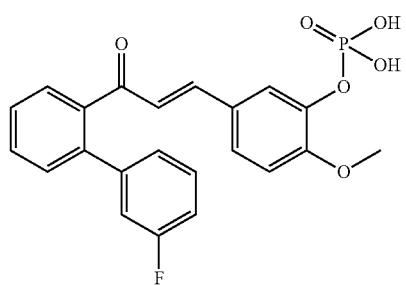
11
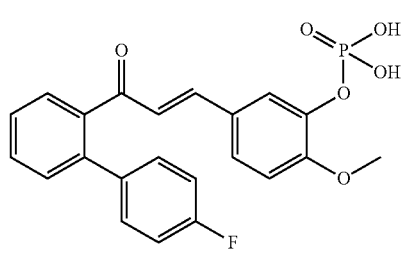
12
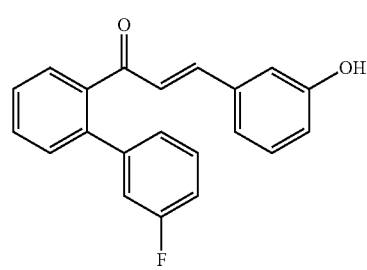
13
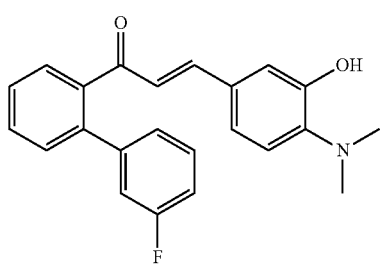
14
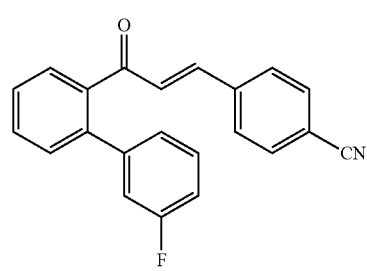
15
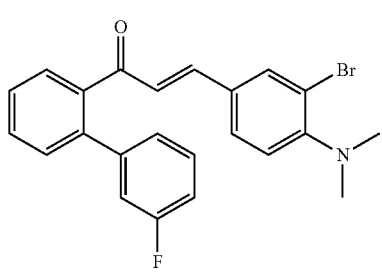
16
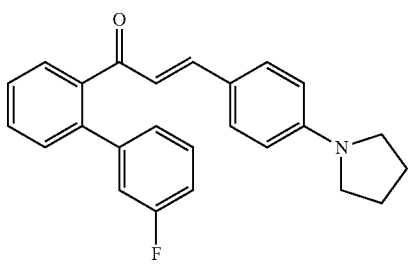
17
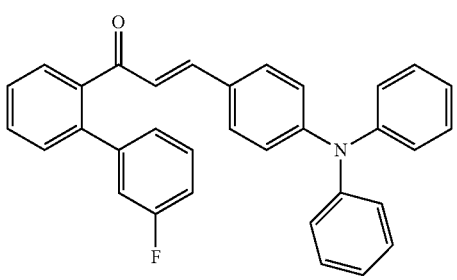
18
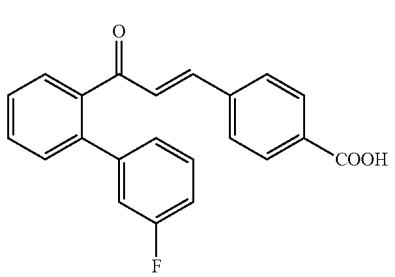
19
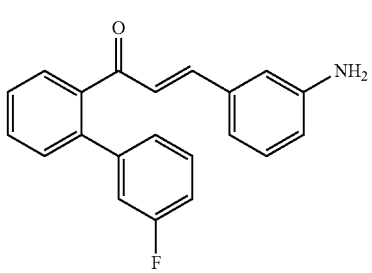
20
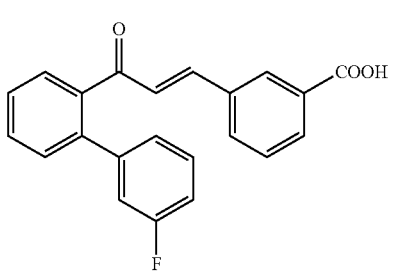
21
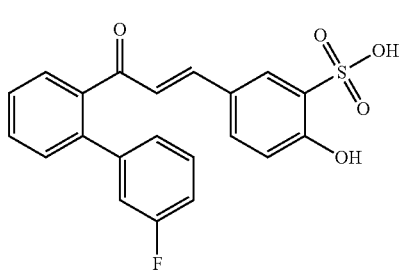

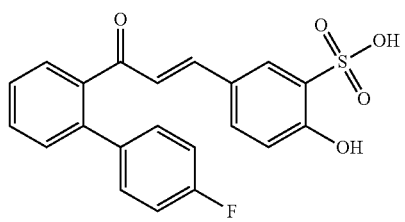

22

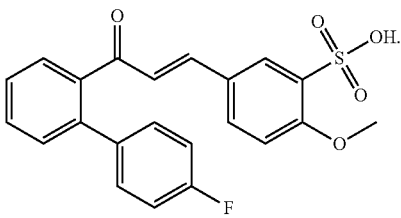

24

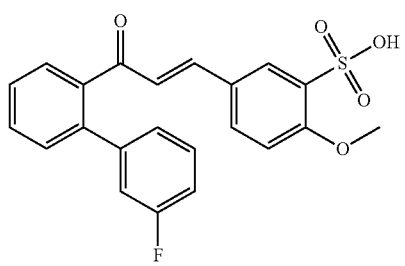

23

2. Pharmaceutically acceptable salts of the o-phenyl chalcone compounds of claim 1.

3. The pharmaceutically acceptable salts of claim 2, including lithium salts, sodium salts, potassium salts, calcium salts, magnesium salts, iron salts, copper salts, organic ammonium salts, hydrochloride, sulfate, phosphate, acetate, propionate, oxalate or citrate.

4. The pharmaceutically acceptable salts of claim 3, wherein the organic ammonium salts include methylamine salts, ethylamine salts, triethylamine salts, and N,N-diisopropylethylamine salts.

\* \* \* \* \*